(12) United States Patent
Ruppert et al.

(10) Patent No.: US 7,851,423 B2
(45) Date of Patent: Dec. 14, 2010

(54) POST-FOAMING CLEANSING PRODUCT WITH MOLECULAR OXYGEN

(75) Inventors: Stephan Ruppert, Hamburg (DE);
Thomas Blatt, Wedel (DE);
Christopher Mummert, Bienenbüettel (DE); Ludger Kolbe, Dohren (DE);
Anja Aechtner, Mannheim (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 12/373,980

(22) PCT Filed: Jun. 25, 2007

(86) PCT No.: PCT/EP2007/056314
§ 371 (c)(1),
(2), (4) Date: Apr. 8, 2009

(87) PCT Pub. No.: WO2008/009539
PCT Pub. Date: Jan. 24, 2008

(65) Prior Publication Data
US 2009/0247444 A1     Oct. 1, 2009

(30) Foreign Application Priority Data
Jul. 19, 2006  (DE) .................. 10 2006 033 797

(51) Int. Cl.
*C11D 1/04*    (2006.01)
*C11D 1/90*    (2006.01)
*C11D 3/20*    (2006.01)
*C11D 3/37*    (2006.01)

(52) U.S. Cl. ............... 510/120; 510/135; 510/140; 510/155; 510/158; 510/475; 510/505; 424/401; 424/70.11; 424/70.21; 424/70.22; 424/70.31

(58) Field of Classification Search ............. 510/120, 510/135, 140, 155, 158, 475, 505; 424/401, 424/70.11, 70.21, 70.22, 70.31
See application file for complete search history.

(56) References Cited

U.S. PATENT DOCUMENTS

| | | | |
|---|---|---|---|
| 4,405,489 | A | 9/1983 | Sisbarro |
| 4,772,427 | A | 9/1988 | Dawson et al. |
| 2004/0022839 | A1 | 2/2004 | Barnikol |
| 2004/0241105 | A1 | 12/2004 | Riedel et al. |
| 2005/0074471 | A1 | 4/2005 | Bleckmann et al. |
| 2007/0031348 | A1 * | 2/2007 | Staeb et al. ............... 424/47 |

FOREIGN PATENT DOCUMENTS

| | | |
|---|---|---|
| DE | 101 13 048 A1 | 9/2002 |
| WO | 02/05754 A2 | 1/2002 |
| WO | 03/022238 A1 | 3/2003 |
| WO | 2005/027869 A1 | 3/2005 |
| WO | WO 2005/027869 * | 3/2005 |

OTHER PUBLICATIONS

Stanzl K. et al., "The effectiveness of molecular oxygen in cosmetic formulations", International Journal of Cosmetic Science, 18, pp. 137-150 (1996).

* cited by examiner

*Primary Examiner*—Brian P Mruk
(74) *Attorney, Agent, or Firm*—Greenblum and Bernstein, P.L.C.

(57) ABSTRACT

Post-foaming cosmetic cleansing preparation on an aqueous basis which is suitable for dispensing from an aerosol container, containing in a conventional aqueous base preparation a) detersive surfactants with saturated radicals, preferably anionic surfactants and non-ionic surfactants and/or amphoteric surfactants, b) 2.5 to 25% by volume, preferably 5 to 20% by volume, particularly preferably 7.5 to 15% by volume of pure oxygen.

15 Claims, No Drawings

POST-FOAMING CLEANSING PRODUCT WITH MOLECULAR OXYGEN

BACKGROUND OF THE INVENTION

1. Field of the Invention

The invention relates to a post-foaming cosmetic cleansing product with molecular oxygen, in particular shower gel or hand-soap gels but also bath concentrates for dispensing from an aerosol container and face cleansing gels.

2. Discussion of Background Information

Cosmetic and dermatological cleansing formulations are known that are packed in compressed gas containers and which foam automatically after application. These formulations comprise a low-viscosity, surfactant-containing cleansing solution that is converted into a cleansing gel through pressurization with high-volatile gases (DE-OS 38 39 349).

Post-foaming cosmetic gels of this type are first applied to the skin in a gel form from the aerosol container with the aid of a discharge means and only then develop the actual foam after a brief delay under the influence of the post-foaming agent contained. The advantage of these compositions compared to the known finished cosmetic foams that are applied to the skin from the aerosol container already foamed, lies in a better wetting of the skin. A decisive disadvantage of these products is that the actual post-foaming process does not start until the consumer foams the product with his hands, because only then does the product clearly increase in volume. Through the time-delayed post-foaming process, an adequate dosage of the cleansing product for the consumer is virtually impossible, and he sometimes removes too much, sometimes too little product.

Post-foaming cosmetic gels are known in principle. U.S. Pat. No. 3,541, cites as essential constituents of a composition of this type water, soap (i.e., water-soluble salts of higher fatty acids), gelling agents and after-foaming agents.

It is furthermore expedient, but not absolutely essential to add cosmetic active ingredients and auxiliary agents. It has also been proposed (U.S. Pat. No. 4,405,489) to omit a gelling agent, but in this case a special and complex process is necessary for the production and filling of compositions of this type.

However, the described post-foaming cosmetic gel preparations have decisive disadvantages, in particular in production: aliphatic hydrocarbons are used as post-foaming agents, preferably n-butane, pentane and hexane. These compounds are combustible and form explosive mixtures with air. Therefore, an increased expenditure for explosion protection and similar safety measures is necessary in production.

The object of the present invention was therefore to create a post-foaming cosmetic gel preparation meeting the requirements from practice, which contains a compound which is not explosive in mixture with air as a post-foaming agent and thus renders possible a less problematic and at the same time also more cost-effective production.

The object of the invention was also to provide further post-foaming cosmetic products on the basis of the post-foaming gel preparation according to the invention, for example, a post-foaming gel for skin care or for skin cleansing.

"Self-foaming," "foam-like," "post-foaming" or "foamable" mean preparations from which foams can in principle be produced—whether already during the production process, during application by the user, on in any other manner—by the incorporation of one or more gases. In foams of this type, the gas bubbles are present distributed (as desired) in one (or more) liquid phase(s), wherein the (foamed) preparations do not necessarily have to have the appearance of a foam macroscopically. (Foamed) cosmetic preparations according to the invention (for the sake of simplicity also referred to below as foams) can represent, e.g., macroscopically visible dispersed systems of gases which are dispersed in liquids. However, the foam character may also be visible, for example, only under a (light) microscope. Furthermore, post-foaming preparations according to the invention—in particular when the gas bubbles are too small to be recognized under a light microscope—are also recognizable by the large increase in volume of the system.

The use of oxygen in cosmetic or dermatological preparations for the prophylaxis and treatment of skin aging phenomena, for example, wrinkles and lines, slackening of the skin and tissue, disturbances in skin regeneration, circulation disorders of the skin, age spots and the like has recently been described (WO 05/27869). However, all of the preparations found there represent emulsions, which are unsuitable for cleansing purposes.

WO 02/05754 describes externally applicable preparations that contain an oxygen carrier that is incorporated into a lipoid emulsion in a molecularly disperse manner, and the use thereof for external treatment/prevention of oxygen deficiency conditions of the skin. However, oxygen carriers are expensive and the emulsions used are not suitable for cleansing purposes.

SUMMARY OF THE INVENTION

The present invention provides a water-based cosmetic cleansing product. The product is post-foaming and suitable for dispensing from an aerosol container and comprises in an aqueous base preparation:

(a) one or more detergent surfactants which comprise saturated groups, and (b) from 2.5% to 25% by volume of pure oxygen.

In one aspect of the product, the one or more detergent surfactants may be selected from one or more of anionic surfactants, non-ionic surfactants, and amphoteric surfactants.

In another aspect, the product may comprise from 5% to 20% by volume, e.g., from 7.5% to 15% by volume of pure oxygen.

In yet another aspect, the product may further comprise at least one gelling agent. Further, the at least one gelling agent may be cross-linked. For example, the at least one gelling agent may comprise at least one of acrylates copolymer, carbomer, and acrylates/C10-30 alkyl acrylate crosspolymer.

In a still further aspect, the product may be free from starch derivatives and/or free from volatile and/or non-volatile hydrocarbons and/or free from unsaturated surfactants and/or free from cationic surfactants.

The present invention also provides a product which is obtained by expanding the cleansing product of the present invention as set forth above (including the various aspects thereof).

The present invention also provides a cosmetic cleansing product which comprises a packaging that comprises an inner deformable and substantially oxygen-tight container and an outer substantially rigid container which is capable of withstanding internal pressure. The inner container contains the cleansing product of the present invention as set forth above (including the various aspects thereof). Further, from 5% to 300% by volume, based on the total volume of the cleansing product inside the inner container, of at least one gas selected from air, nitrogen, helium, argon, laughing gas, and carbon dioxide is present between the inner container and the outer container and under a pressure which is suitable for dispensing the cleansing product inside the inner container.

In one aspect of the cleansing product, the at least one gas may comprise air.

The present invention also provides methods of improving the appearance of skin and/or skin appendages and/or of increasing the microcirculation of skin and/or of improving the color of skin and the complexion and/or of improving the softness of skin and/or of improving the elasticity of skin, hair and/or nails and/or of increasing the radiance of skin and/or of increasing or restoring the barrier properties of skin and/or of protecting skin from drying and/or of protecting skin from environmental effects and/or of protecting skin of children and adolescents and/or of increasing skin cell regeneration and/or of refreshing the skin renewal effect and/or of rejuvenating the skin cell structure. All of these methods comprise the application of the cleansing product of the present invention as set forth above (including the various aspects thereof) to the skin.

DETAILED DESCRIPTION OF THE INVENTION

It has surprisingly been found that a post-foaming cosmetic cleansing preparation on an aqueous basis which is suitable for dispensing from an aerosol container, containing in a conventional aqueous base preparation a) detersive surfactants with saturated radicals, preferably anionic surfactants (very particularly preferably LES, MES, sodium cocoyl glutamate, sodium methyl cocoyltaurate, disodium PEG-5 laurylcitrate sulfosuccinate) and non-ionic surfactants (very particularly preferably APGs, PEG-7 glyceryl cocoate) and/or amphoteric (very particularly preferably cocamidopropyl betaine) surfactants and b) 2.5 to 25% by volume, preferably 5 to 20% by volume, particularly preferably 7.5 to 15% by volume of pure oxygen, remedies the disadvantages of the prior art. Post-foaming cleansing products of this type that contain compressed molecular oxygen, foam to their final volume immediately after removal and thus facilitate the dosing for the consumer considerably. Moreover, it has surprisingly been found that the molecular oxygen contained in the cleansing formulation penetrates into the skin during the application and causes a particular effect there. Surprisingly, a very even and thin distribution of the product on the skin is achieved through the very fine foam. This leads to an extraordinarily pleasant smooth and velvety feeling on the skin that is unusual for an aqueous cleansing product during and after the application of the product. The preparations according to the invention thus in every respect represent extremely satisfactory preparations. The invention also comprises a foamed preparation that can be obtained by expanding a preparation described above.

It is preferred when, in addition, a gelling agent is used.

It is preferred when the gelling agent is cross-linked and is particularly preferably selected from the group acrylates copolymer, carbomer, acrylates/C10-30 alkyl acrylate crosspolymer.

It is preferred when the preparation is free from starch derivatives.

It is preferred when the preparation is free from volatile and/or nonvolatile hydrocarbons.

It is preferred when the preparation is free from unsaturated surfactants.

It is preferred when the preparation is free from cationic surfactants.

It is preferred when the preparation is present as a foam after expansion.

Furthermore, it was possible to prove through experiments on suction blisters that the oxygen penetrates into the skin, even if water is added, which always occurs during showering. To this end, suction blisters (Ø 5 mm) were generated on the volar forearm of test subjects by the application of a vacuum (see: Kuhn M, Wolber R, Kolbe L, Schnorr O, Sies H., Solar-simulated radiation induces secretion of IL-6 and production of isoprostanes in human skin in vivo, Arch Dermatol Res. 2006 April; 297 (10): 477-9). An oxygen electrode (Needle Type Fiber-Optic Oxygen Microsensor/Microx TX3, PreSens GmbH, Regensburg) was inserted into the suction blister and positioned under the roof of the suction blister. The concentration of oxygen inside the suction blister was measured with the aid of the O2 electrode and the increase (difference) between the control value (before product application) and the product application (in mg/L) was determined.

The product is transparent for a fraction of a second after application from the packaging and then exhibits striae. The oxygen is present in the form of small gas beads.

A cosmetic cleansing product is also according to the invention that comprises a packaging with an inner deformable and substantially oxygen-tight container containing a preparation according to one of the preceding claims and an outer essentially rigid container that can withstand the internal pressure, wherein between the inner and outer container 5 to 300% by volume based on the total volume of the preparation in the inner container, of a gas (primary propellant), chosen from the group of air, nitrogen, helium, argon, laughing gas and carbon dioxide, preferably air is present under a pressure which is suitable for application of the preparation in the inner container. The preparation is thereby present in a container that is pressurized by the primary propellant, so that the preparation is released upon opening the container.

Surprisingly, it has been shown that upon the gassing of the cleansing product with oxygen in a HANSA mixer an oxygen-enriched gel is formed, and not—as would have been expected—a foam that would not be accessible for a filling.

The outer packaging can be preferably of aluminum (with a protective coating).

In view of pumpability, it is advantageous if the viscosities of the cleanser formulations to be gassed do not exceed 6000 mPas (measured with the Haake Viscotester VT-02 at 20° C.).

Preparations or products according to the invention are used to improve the appearance of the skin and/or cutaneous appendages, in particular to increase the microcirculation of the skin, to improve the color of the skin and the complexion, to improve the softness of the skin, to increase the radiance of the skin, to improve the elasticity of skin, hair and/or nails, to increase or restore the barrier properties of the skin, to protect the skin from drying, to protect the skin from environmental effects, to protect the skin of children and adolescents, to increase skin cell regeneration, to refresh the skin renewal effect, to rejuvenate the skin cell structure.

EXAMPLES

The following raw materials were used:

| | |
|---|---|
| Acrylates/C10-30 Alkyl Acrylate Crosspolymer | Carbopol ETD 2020 (Noveon) |
| Hydroxypropyl Starch Phosphate | Structure XL (National Starch) |
| Styrene/Acrylates Copolymer | Acusol OP 301 (Rohm & Haas) |
| Polyethylene | Inducos 14/1 HN (Induchem) |
| Acrylates Copolymer | Aqua SF-1 (Noveon) |
| Carbomer | PAS 80 (Noveon) |

|  | Shower gels | | | | |
| --- | --- | --- | --- | --- | --- |
|  | 1 | 2 | 3 | 4 | 5 |
| Sodium lauryl ether sulfate | 13.2 | 11 | 9.5 | 11 | 9.5 |
| Cocoamidopropyl Betaine | 1.65 | 3.3 | 3.8 | 4 | 5 |
| Sodium cocoyl glutamate | 1.25 | 0.75 | 2.5 | 2.5 | 1 |
| PEG-7 Glyceryl Cocoate | 2.5 | 1.5 | 2 | 2 | 1.5 |
| Acrylate Copolymer | — | — | — | 2.2 | 2.6 |
| PEG-40 hydrogenated castor oil | 0.4 | 0.5 | 0.8 | 0.7 | 0.9 |
| PEG-200 hydrogenated glyceryl palmitate | 0.1 | 0.5 | 0.3 | — | — |
| Polyquaternium-10 | — | 0.2 | 0.2 | — | 0.1 |
| Ethylene glycol distearate | 1.5 | — | — | — | — |
| Styrene/Acrylates Copolymer | — | — | 0.9 | — | 1 |
| Sodium chloride | — | 0.2 | 0.2 | — | — |
| Sodium benzoate | 0.4 | 0.4 | 0.4 | — | — |
| Sodium salicylate | 0.4 | 0.4 | 0.4 | — | — |
| Citric acid | q.s. | q.s. | q.s. | — | — |
| Phenoxyethanol | — | — | — | 0.6 | 0.6 |
| Methyl paraben | — | — | — | 0.4 | 0.3 |
| Propyl paraben | — | — | — | 0.2 | 0.3 |
| Aqueous sodium hydroxide | — | — | — | q.s. | q.s. |
| Perfume | q.s. | q.s. | q.s. | q.s. | q.s. |
| Water | ad 100 | ad 100 | ad 100 | ad 100 | ad 100 | pH adjusted to 4.8-7

To produce the foam, 85% by volume of the formulation is foamed up with 15% by volume of oxygen.[a]

[a] The foaming up can occur, e.g., in that gas is blown into the preparations or they are (strongly) beaten, shaken, sprayed or stirred in the respective gas atmosphere.

|  | 6 | 7 | 8 | 9 | 10 | 11 |
| --- | --- | --- | --- | --- | --- | --- |
| Sodium lauryl ether sulfate | 5.5 | 6 | 7 | 5 | 6 | 5.5 |
| Cocoamidopropyl betaine | 5.5 | 5 | 4 | — | 5 | 5.5 |
| Sodium cocoyl glutamate | — | — | 1 | 1.5 | 1 | — |
| PEG-7 Glyceryl cocoate | — | 2 | — | — | 2 | 1.5 |
| Acrylate Copolymer | — | — | — | — | 2 | 2.4 |
| Polyquaternium-10 | — | — | 0.2 | — | — | 0.2 |
| Polyquaternium-7 | — | 0.3 | — | — | — | — |
| Ethylene glycol distearate | 1.2 | — | — | 1 | — | 1.2 |
| Styrene/Acrylates Copolymer | — | 1 | — | — | — | — |
| PEG-200 hydrogenated glyceryl palmitate | 1 | 1 | 0.8 | 0.8 | — | 0.2 |
| PEG-40 hydrogenated castor oil | 0.4 | 0.4 | 0.4 | 0.3 | 0.3 | 0.4 |
| Sodium chloride | 0.3 | 0.1 | 0.3 | 0.3 | — | — |
| Sodium salicylate | 0.4 | 0.4 | 0.3 | 0.4 | — | — |
| Sodium benzoate | 0.4 | 0.5 | 0.5 | 0.4 | — | — |
| Citric acid | q.s. | q.s. | q.s. | q.s. | — | — |
| Phenoxyethanol | — | — | — | — | 0.7 | 0.6 |
| Methyl paraben | — | — | — | — | 0.3 | 0.4 |
| Propyl paraben | — | — | — | — | 0.3 | 0.4 |
| Aqueous sodium hydroxide | — | — | — | — | q.s. | q.s. |
| Perfume | q.s. | q.s. | q.s. | q.s. | q.s. | q.s. |
| Water | ad 100 | ad 100 | ad 100 | ad 100 | ad 100 | ad 100 | pH adjusted to 4.8-7

To produce the foam, 90% by volume of the formulation is foamed up with 10% by volume of oxygen.[a]

| Face cleansing gels | | | | | |
|---|---|---|---|---|---|
| | 12 | 13 | 14 | 15 | 16 |
| Sodium myreth sulfate | 3 | 3.5 | 2 | 2.5 | 4 |
| Lauryl glucoside | 1 | 2 | 1.5 | 0.8 | — |
| Cocamidopropyl betaine | 4 | 2 | 3 | 3.5 | 5 |
| Acrylates Copolymer | 2.3 | 2.3 | 2 | 2.5 | 3 |
| Ethylene glycol distearate | 1.5 | — | — | — | — |
| Styrene/Acrylates Copolymer | — | 2 | 1 | — | — |
| PEG-200 hydrogenated glyceryl palmitate | 0.2 | 0.5 | — | 0.7 | — |
| PEG-40 hydrogenated castor oil | 0.5 | 0.4 | 0.3 | 0.4 | 0.6 |
| Polyquaternium-10 | — | 0.2 | — | 0.1 | — |
| Methyl paraben | 0.3 | 0.4 | 0.3 | 0.4 | 0.3 |
| Propyl paraben | 0.3 | 0.4 | 0.3 | 0.2 | 0.3 |
| Phenoxyethanol | 0.6 | 0.6 | 0.6 | 0.6 | 0.6 |
| Polyethylene | 1.5 | — | — | 0.5 | — |
| Trisodium EDTA | 0.5 | 0.3 | 0.3 | 0.5 | — |
| Sodium hydroxide | q.s. | q.s. | q.s. | q.s. | q.s. |
| Perfume | q.s. | q.s. | q.s. | q.s. | q.s. |
| Water | ad 100 | ad 100 | ad 100 | ad 100 | ad 100 | pH adjusted to 6.5-7

To produce the foam, 80% by volume of the formulation is foamed up with 20% by volume of oxygen.[a]

| | 17 | 18 | 19 | 20 | 21 |
|---|---|---|---|---|---|
| Sodium lauryl ether sulfate | 1.5 | 2 | 1 | 2.5 | 1.5 |
| Sodium methyl cocoyltaurate | 0.6 | 0.5 | 0.9 | 1 | 0.5 |
| Decyl glucoside | 0.3 | 0.2 | — | — | 0.5 |
| PEG-7 glyceryl cocoate | 0.6 | 0.5 | — | 0.7 | 0.4 |
| Carbomer | 1.2 | 1.2 | 1.2 | 1.2 | 1.2 |
| Glycerin | 2 | 2 | 2 | 2 | 2 |
| PEG-40 hydrogenated castor oil | — | — | — | 0.4 | 0.6 |
| Xanthan gum | 0.25 | 0.25 | 0.25 | 0.25 | 0.25 |
| Styrene/Acrylates Copolymer | — | — | 1 | 2 | — |
| Parabens | 0.3 | 0.4 | 0.3 | 0.3 | 0.4 |
| Phenoxyethanol | 0.7 | 0.6 | 0.7 | 0.7 | 0.6 |
| Sodium hydroxide | q.s. | q.s. | q.s. | q.s. | q.s. |
| Perfume | q.s. | q.s. | q.s. | q.s. | q.s. |
| Water | ad 100 | ad 100 | ad 100 | ad 100 | ad 100 | pH adjusted to 6.2-7.1

To produce the foam, 75% by volume of the formulation is foamed up with 25% by volume of oxygen.[a]

| | 22 | 23 | 24 | 25 | 26 |
|---|---|---|---|---|---|
| Sodium myreth sulfate | 1.8 | 2 | 2.5 | 2.2 | 2.5 |
| Decyl glucoside | 2.2 | 2 | 1.8 | 2 | 2 |
| Cocoamidopropyl betaine | 3.5 | 3.5 | 4 | 3 | 4 |
| Acrylates/C10-30 Alkyl Acrylate Crosspolymer | 0.6 | 0.8 | 0.7 | 0.9 | 1 |
| Hydroxypropyl starch phosphate | 0.8 | 0.9 | 1 | — | 0.9 |
| PEG-40 hydrogenated castor oil | 0.5 | 0.5 | — | 0.3 | 0.4 |
| PEG-90 glyceryl isostearate + laureth-2 | 0.2 | 0.2 | 0.1 | 0.15 | — |
| Polyquaternium-10 | — | 0.1 | 0.1 | — | — |
| Styrene/Acrylates Copolymer | 1 | — | 2 | — | — |
| Polyethylene | 2 | — | — | 0.5 | — |
| Phenoxyethanol | 1 | 1 | 0.9 | 0.9 | 1 |
| Methyl paraben | 0.4 | 0.3 | 0.4 | 0.4 | 0.3 |

-continued

|  | 22 | 23 | 24 | 25 | 26 |
|---|---|---|---|---|---|
| Propyl paraben | 0.4 | 0.2 | 0.4 | 0.4 | 0.3 |
| Sodium hydroxide | q.s. | q.s. | q.s. | q.s. | q.s. |
| Perfume | q.s. | q.s. | q.s. | q.s. | q.s. |
| Water | ad 100 | ad 100 | ad 100 | ad 100 | ad 100 | pH adjusted to 5.9-6.5

To produce the foam, 85% by volume of the formulation is foamed up with 15% by volume of oxygen.$^a$

| Shampoos: | | | | | | |
|---|---|---|---|---|---|---|
|  | 27 | 28 | 29 | 30 | 31 | 32 |
| Sodium lauryl ether sulfate | 10 | 9 | 8 | 9 | 9 | 9.5 |
| Cocamidopropyl betaine | 3 | 4 | 3 | 4 | 3 | 3 |
| Disodium PEG-5 lauryl citrate sulfosuccinate | 4 | — | 2 | 3 | — | — |
| Polyquaternium-10 | 0.3 | 0.2 | 0.1 | 0.3 | 0.2 | 0.1 |
| Guar hydroxypropyl-trimonium chloride | 0.1 | — | 0.1 | 0.2 | | — |
| PEG-3 distearate | 1.5 | 3 | 4 | 2 | 1.5 | — |
| PEG-40 hydrogenated castor oil | 0.4 | 0.3 | 0.3 | 0.4 | 0.6 | 0.6 |
| Sodium salicylate | 0.4 | 0.4 | 0.4 | 0.4 | 0.2 | — |
| Sodium benzoate | 0.4 | 0.4 | 0.4 | 0.4 | 0.4 | 0.45 |
| Sodium chloride | 1.5 | 1.0 | 1.2 | 1.0 | 2.0 | 1.0 |
| Citric acid | q.s. | q.s. | q.s. | q.s. | q.s. | q.s. |
| Perfume | q.s. | q.s. | q.s. | q.s. | q.s. | q.s. |
| Water | ad 100 | ad 100 | ad 100 | ad 100 | ad 100 | ad 100 | pH adjusted to 4.8-5.8

To produce the foam, 80% by volume of the formulation is foamed up with 20% by volume of oxygen.$^a$

What is claimed is:

1. A cosmetic cleansing product, wherein the product is water-based, post-foaming and suitable for dispensing from an aerosol container and comprises in an aqueous base preparation:
    (a) one or more detergent surfactants which comprise saturated groups, comprising at least one surfactant selected from lauryl ether sulfates, myreth sulfates, sodium cocoyl glutamate, sodium methyl cocoyltaurate, and disodium PEG-5 laurylcitrate sulfosuccinate; and
    (b) from 2.5% to 25% by volume of pure oxygen.

2. The cleansing product of claim 1, wherein the one or more detergent surfactants comprise at least one anionic surfactant.

3. The cleansing product of claim 1, wherein the one or more detergent surfactants comprise at least one amphoteric surfactant.

4. The cleansing product of claim 1, wherein the one or more detergent surfactants comprise at least one non-ionic surfactant.

5. The cleansing product of claim 1, wherein the one or more detergent surfactants comprise at least one surfactant selected from alkyl polyglucosides, alkyl glucosides, PEG-7 glyceryl cocoate, and cocoamidopropyl betaine.

6. The cleansing product of claim 1, wherein the product comprises from 5% to 20% by volume of pure oxygen.

7. The cleansing product of claim 1, wherein the product further comprises at least one gelling agent.

8. The cleansing product of claim 7, wherein the at least one gelling agent is cross-linked.

9. The cleansing product of claim 7, wherein the at least one gelling agent comprises at least one of acrylates copolymer, carbomer, and acrylates/C10-30 alkyl acrylate crosspolymer.

10. A foamed product which is obtained by expanding the cleansing product of claim 1.

11. A cosmetic cleansing product, wherein the product is water-based, post-foaming and suitable for dispensing from an aerosol container and comprises in an aqueous base preparation:
    (a) one or more detergent surfactants which comprise at least one of an anionic surfactant and an amphoteric surfactant and comprise at least one surfactant selected from lauryl ether sulfates, myreth sulfates, sodium cocoyl glutamate, sodium methyl cocoyltaurate, disodium PEG-5 laurylcitrate sulfosuccinate, and cocoamidopropyl betaine;
    (b) from 7.5% to 15% by volume of pure oxygen; and
    (c) a gelling agent which comprises at least one of acrylates copolymer, carbomer, and acrylates/C10-30 alkyl acrylate crosspolymer.

12. A cosmetic cleansing product, wherein the product comprises a packaging comprising an inner deformable and oxygen-tight container and an outer rigid container which is capable of withstanding internal pressure, the inner container containing the cleansing product of claim 1, and wherein from 5% to 300% by volume, based on a total volume of the cleansing product inside the inner container, of at least one gas selected from air, nitrogen, helium, argon, laughing gas, and carbon dioxide is present between the inner container and the outer container and under a pressure which is suitable for dispensing the cleansing product inside the inner container.

13. The cleansing product of claim 12, wherein the at least one gas comprises air.

14. A method of at least one of improving the appearance of skin and/or skin appendages, increasing the microcirculation of skin, improving the color of skin and the complexion, improving the softness of skin, improving the elasticity of skin, hair and/or nails, and increasing the radiance of skin, wherein the method comprises applying to skin, skin appendages, hair and/or nails the cleansing product of claim 1.

15. A method of at least one of increasing or restoring the barrier properties of skin, protecting skin from drying, protecting skin from environmental effects, protecting skin of children and adolescents, increasing skin cell regeneration, refreshing the skin renewal effect, and rejuvenating the skin cell structure, wherein the method comprises applying to skin the cleansing product of claim 1.

* * * * *